US00PP21966P3

(12) United States Plant Patent
Holland et al.

(10) Patent No.: US PP21,966 P3
(45) Date of Patent: Jun. 7, 2011

(54) POMEGRANATE TREE NAMED 'KAMEL'

(50) Latin Name: *Punica granatum*
Varietal Denomination: KAMEL

(75) Inventors: Doron Holland, Hasolelim (IL); Irit Bar-Ya'Akov, Qiryat Tivon (IL); Kamel Hatib, Arrabe (IL)

(73) Assignee: State of Israel, Ministry of Agriculture & Rural Development, Agricultural Research Organization, Bet Dagan (IL)

( * ) Notice: Subject to any disclaimer, the term of this patent is extended or adjusted under 35 U.S.C. 154(b) by 16 days.

(21) Appl. No.: 12/462,240

(22) Filed: Jul. 31, 2009

(65) Prior Publication Data

US 2011/0030111 P1 Feb. 3, 2011

(51) Int. Cl.
*A01H 5/00* (2006.01)

(52) U.S. Cl. ..... Plt./210

(58) Field of Classification Search ..... Plt./210
See application file for complete search history.

(56) References Cited

OTHER PUBLICATIONS

UPOV ROM GTITM Computer Database, GTI Jouve Retrieval Software 2010/03 Citation for 'KAMEL'.*
Print-out of application Number and filing date information for corresponding IL PBR application No. 4030/07 filed Apr. 10, 2007, published by the Ministry of Agriculture & Rural Development in Israel PBR Gazette No. 69, Jan. 1, 2007 —Jun. 30, 2007 (4 pages). (http://www.moag.gov.il/NR/rdonlvres/DA946C0C-4AA5-4A6A-8B31-D8A43DBAC5DF/0/1176gazette69_160807.pdf).
Print-out of application Number and filing date information from Community Plant Variety Office (CPVO) website for corresponding, CPVO application No. 2007/2596 filed Nov. 26, 2007 (5 pages). (http://www.cpvoextranet.cpvo.europa.eu).

* cited by examiner

*Primary Examiner* — Wendy C. Haas
(74) *Attorney, Agent, or Firm* — Foley & Lardner LLP

(57) ABSTRACT

A new and distinct pomegranate variety of *Punica granatum* named 'KAMEL', particularly characterized by self-pollinating and self-fertile medium-sized tree with vigorous growth; good fruit productivity; large-sized, mature fruit with uniform, dark red skin color that appears very early in fruit development, red arils; and mature fruit which is of good eating quality, sweet-sour flavor and good juice production.

6 Drawing Sheets

Botanical name of the genus and species of the plant claimed: *Punica granatum* L.

Variety denomination: 'KAMEL'.

BACKGROUND OF THE INVENTION

The present invention relates to a new and distinct variety of a pomegranate tree, botanically known as *Punica granatum* L. of the Lythraceae family, and hereinafter referred to by the variety denomination 'KAMEL'.

The new *Punica granatum* 'KAMEL' is a product of a controlled breeding program conducted by the inventors, Doron Holland, Irit Bar-Ya'akov and Kamel Hatib in the Yizre'el Valley, Israel. The objective of the breeding program was to develop a new *Punica granatum* variety with vigorous production of mature fruit and good eating quality.

Pomegranate seedlings were collected from different sites (in Israel) and planted in the Yizre'el Valley, Israel. The new *Punica granatum* 'KAMEL' originated from open pollination of an unknown *Punica granatum* variety. The new *Punica granatum* 'KAMEL' was observed in 2003 and selected in 2006 by the inventors in a controlled environment in Yizre'el Valley, Israel.

Asexual propagation of the new *Punica granatum* 'KAMEL' by cuttings was first performed in February 2006 in the Yizre'el Valley of Israel, and has demonstrated that the combination of characteristics as herein disclosed for the new variety is firmly fixed and retained through successive generations of asexual propagation. The new variety propagates true-to-type. Resulting plants of the new *Punica granatum* were planted in 2007 in the Yizre'el Valley.

BRIEF DESCRIPTION OF THE INVENTION

The following traits have been repeatedly observed and are determined to be characteristics of 'KAMEL' which in combination distinguish this pomegranate tree as a new, unique and distinct variety:

1. Self-pollinating and self-fertile medium-sized tree with vigorous growth;
2. Good fruit productivity;
3. large-sized mature fruit with uniform dark red skin color that appears very early in fruit development,
4. red arils; and
5. mature fruit which is of good eating quality, sweet-sour flavor and good juice production.

Of the many commercial varieties known to the present inventor, the most similar in comparison to the new *Punica granatum* 'KAMEL' is *Punica granatum* 'WONDERFUL' (unpatented), in the following characteristics described in Table 1:

TABLE 1

| Characteristic | New Variety 'KAMEL' | Comparison Variety 'WONDERFUL' (unpatented) |
|---|---|---|
| Ripening time | Late (beginning of October) | Late (beginning of October) |

TABLE 1-continued

| Characteristic | New Variety 'KAMEL' | Comparison Variety 'WONDERFUL' (unpatented) |
|---|---|---|
| Mature fruit skin color | Dark red | Red |
| Timing of full red skin color appearance | Early fruit in developmental stages before fruit matures | Mature fruit |

BRIEF DESCRIPTION OF THE PHOTOGRAPHS

The accompanying photographs illustrate the overall appearance of the new *Punica granatum* 'KAMEL', showing the colors as true as is reasonably possible with colored reproductions of this type. Colors in the photographs may differ slightly from the color values cited in the detailed botanical description, which accurately describe the color of 'KAMEL'.

DETAILED BOTANICAL DESCRIPTION

Figure 1:
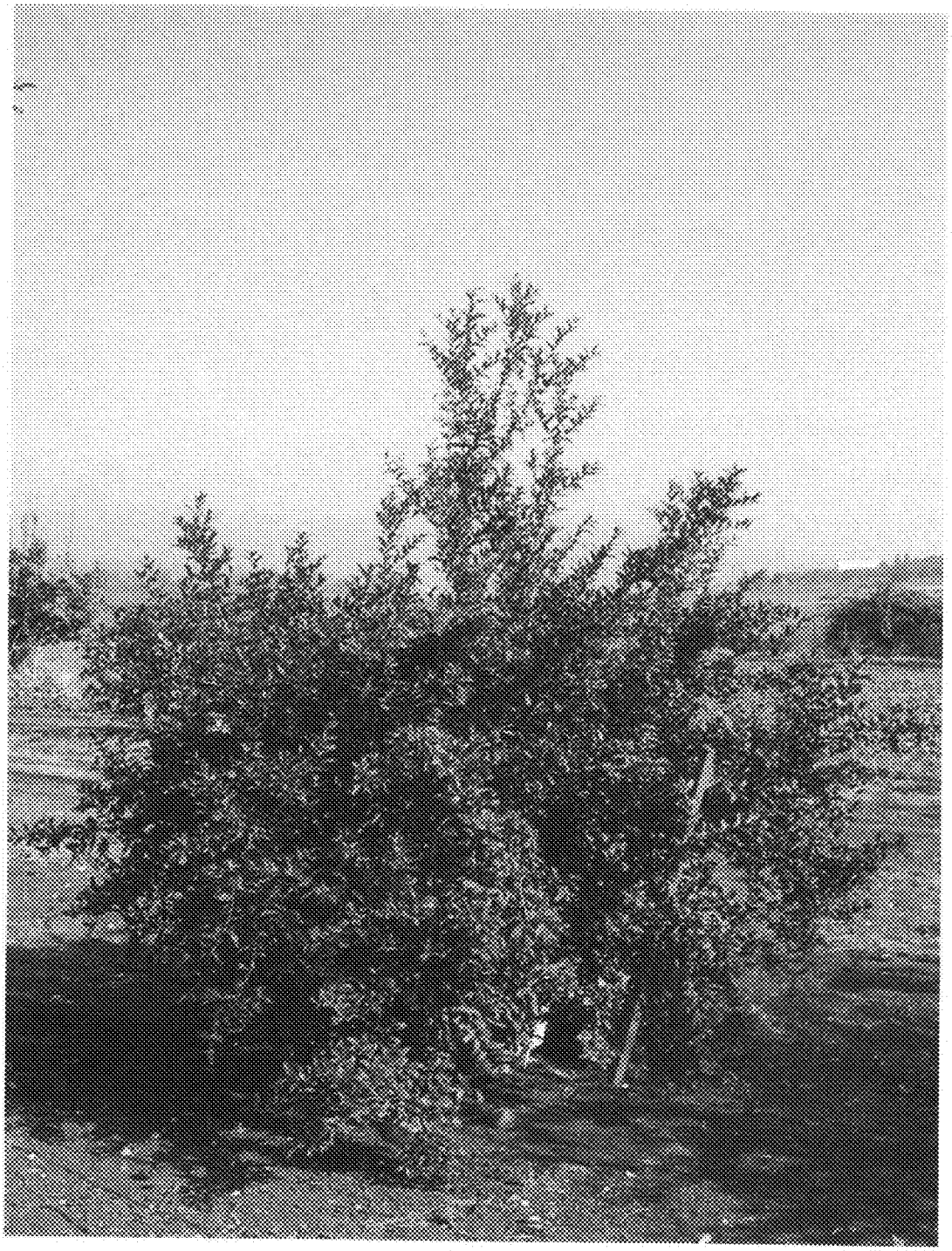
FIG. 1 shows a side view perspective of a typical 3 year old shrub of 'KAMEL'.
Figure 2:
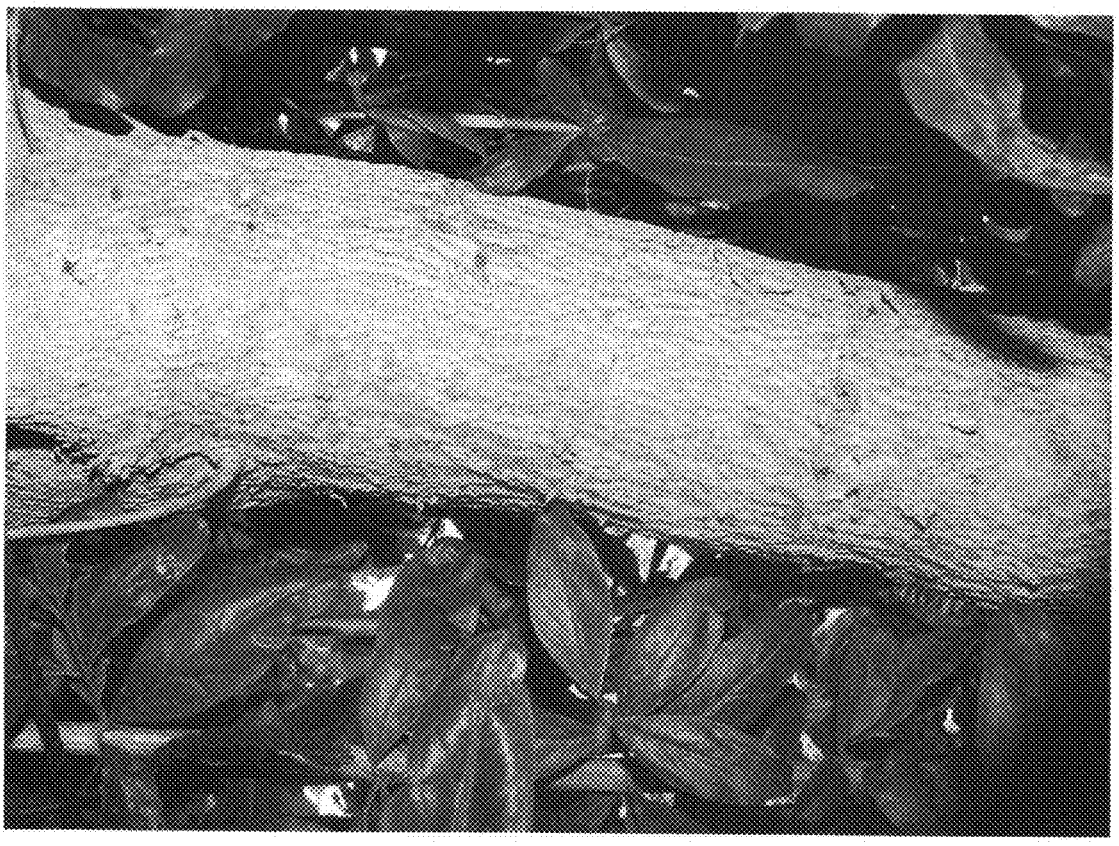
FIG. 2 shows a side view perspective of a typical trunk of 'KAMEL'.
Figure 3:
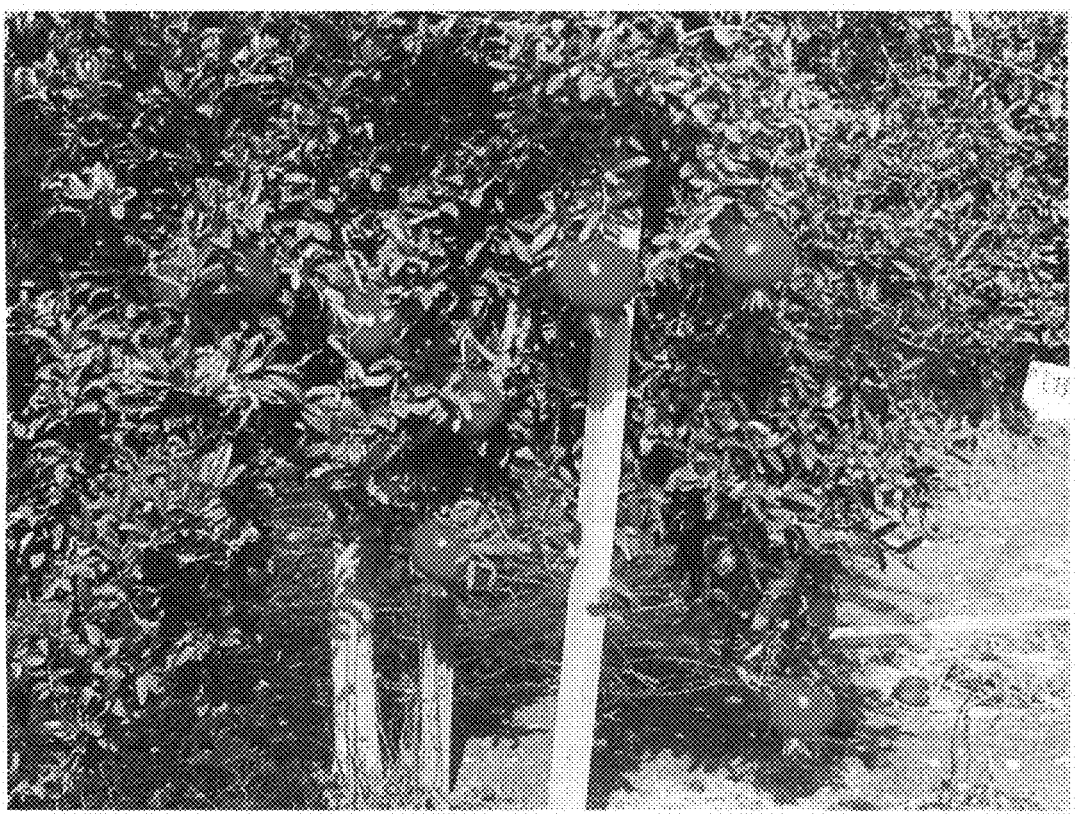
FIG. 3 shows a close-up view of typical fruit on a branch of 'KAMEL'.
Figure 4:
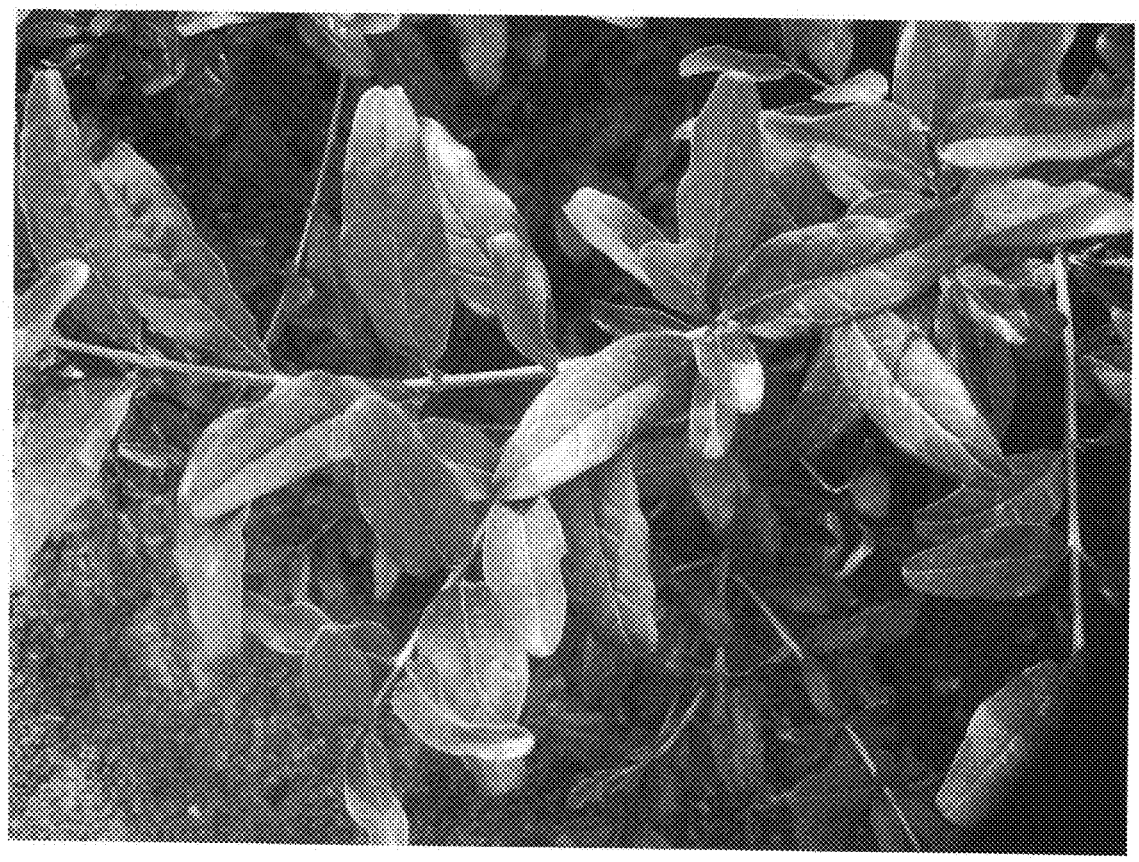
FIG. 4 shows a close-up view of typical leaves of 'KAMEL'.
Figure 5:
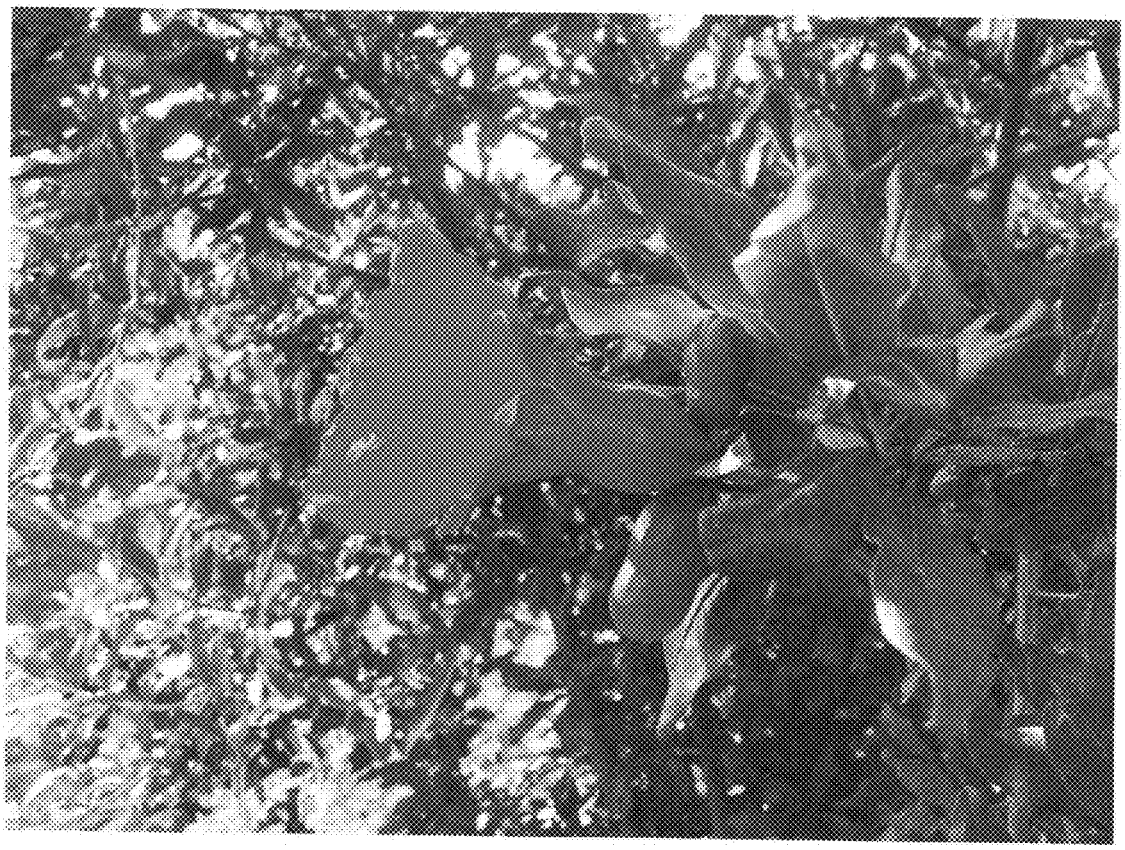
FIG. 5 shows a close-up view of typical hermaphrodite flower of 'KAMEL'.
Figure 6:
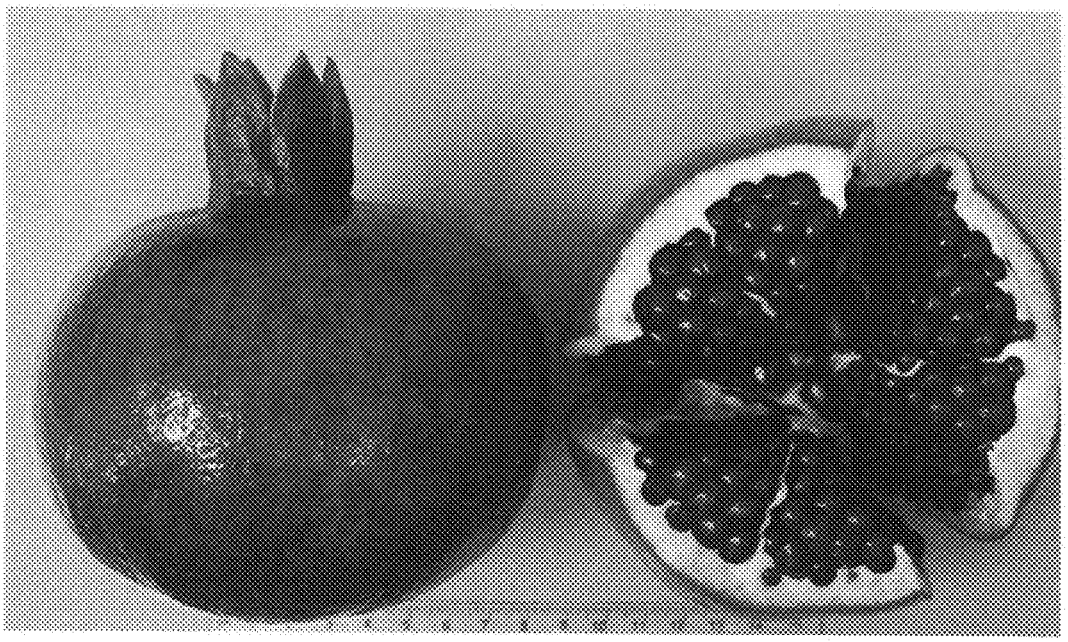
FIG. 6 shows various close-up views of typical mature fruit of 'KAMEL', illustrating the skin and arils color and fruit shape.

The new *Punica granatum* 'KAMEL' has not been observed under all possible environmental conditions. The phenotype of the new variety may vary with variations in environment such as temperature, light intensity, and day length without any change in the genotype of the pomegranate tree.

The aforementioned photographs, together with the following observations, measurements and values describe trees of 'KAMEL' as grown in the pomegranate farm in the Yizre'el Valley of Israel, under conditions which closely approximate those generally used in commercial practice. Seedlings of 'KAMEL' were planted in clay grumusol (vertisol) soil at an elevation of about 100 meters above sea level, at lat. 32°42'N, long. 35°11'E. Yizre'el Valley is characterized by a Mediterranean subtropical climate, with an average annual rainfall of about 580 mm concentrated from November through March. Mean diurnal minimum temperature in January is 6° C. (43° F.), and mean diurnal maximum temperature in July is 33° C. (91° F.).

Unless otherwise stated, the detailed botanical description includes observations, measurements and values based on two-year-old 'KAMEL' trees grown in the pomegranate farm in Yizre'el Valley, Israel from 2006 to 2008. Quantified measurements are expressed as an average of measurements taken from a number of trees of 'KAMEL'. The measurements of any individual tree, or any group of trees, of the new variety may vary from the stated average.

Color references are made to The Royal Horticultural Society Colour Chart (R.H.S.), 2001 edition, except where general colors of ordinary significance are used. Color values were taken under daylight conditions at approximately late morning in Yizre'el Valley, Israel.

All of the trees of 'KAMEL', insofar as they have been observed, have been consistent in all the characteristics described below.

Classification:

*Botanical.*—*Punica granatum* L.

Parentage: Open-pollination of unknown *Punica granatum* variety.

Propagation: cuttings

Growing conditions:

*Light intensities.*—Full sunlight.

*Fertilization.*—A level of about 250 Kg/ha N and 300 Kg/ha K per year and about 60 Kg/ha P every three years.

*Growth regulators.*—Not used.

*Pruning or trimming requirements.*—Winter pruning and removal of suckers during summer.

Tree:

Type: Deciduous

*Age.*—Observed trees were two years old.

*Vigor.*—Good.

*Form.*—Upright and spreading; medium-sized tree with one trunk.

*Branching habit.*—Main branches angle is up to 45° with respect to trunk if allowed to grow naturally.

*Production.*—Good.

*Size at maturity.*—Height: 2.2 m to 2.8 m. Spread: 2.6 to 3.1 m.

*Trunk.*—Height (up to leaders): 30-40 cm. Diameter (20 cm above ground): 28.2 cm±3.0 cm. Texture: Rough. Bark color: Brown, RHS N200C. Trunk Lenticels: None.

*Branches.*—Number per tree: 4 or 5 depending on pruning. Length: 2 m to 3 m. Diameter (at two years, 20 cm above branching): 14.7 cm±0.8 cm. Growth per season: On average, branches grow up to 2 m per growing season. New branchlets form, radiating from the older, primary branch.

*Surface texture.*—New Growth: Semi-rough. Mature: Rough.

*Color.*—New Growth: Grey-brown, RHS 199A. Mature: Brown, RHS N200B.

*Internode length.*—40 mm to 53 mm.

*Internode diameter.*—4 mm to 5 mm. Branch spines: Length: 3 mm to 8 mm. Diameter: About 1 mm. Color: Brown, RHS 174 A. Branch lenticels: None.

*Spur.*—Present. Distance between each spur: Varies. Thickness of each spur: 3 mm to 4 mm. Number of fruit per spur: 1 or 2.

Foliage:

*Arrangement.*—Opposite, pairs alternately crossing at right angles, petiolated.

*Leaf Blade:*—Size (fully developed Leaf Blade): Length: 7.2 cm±0.3 cm. Width: 2.1 cm±0.1 cm. Overall shape: Oblanceolate. Base shape: Acuminate. Apex shape: Obtuse. Margin: Entire. Texture: Upper surface: Smooth. Lower surface: Smooth. Color (mature leaves): Upper surface: Green, RHS 137 A. Lower surface: Green, RHS 137 C. Color (immature leaves): Upper and lower surfaces: Reddish.

*Venation.*—Type: Pinnate. Color: Green midrib, RHS 137C, about 1 mm in thickness.

*Petiole.*—Length: 6.2 mm±0.4 mm. Diameter: About 1.0 mm. Color: Green, RHS 137 C.

*Stipule.*—Exstipulate.

*Glands.*—None.

Inflorescence:

*Time of flowering:*—Full flowering beginning of May in Yizre'el Valley, Israel.

*Flowering period:*—About one month.

*Fragrance.*—None.

*Inflorescence.*—Length: Up to 15 cm. Type: Hermaphrodite flowers are born single or clustered. The flowers can be found on the same plant in various shapes and size. There are vase-shaped flowers with fully developed reproductive organs and bell-shaped flowers which have undeveloped reproductive organs, and between these two types there are various flower shapes and stages of development. The flower described herein is a fully developed flower.

*Flower diameter.*—33 mm to 41 mm.

*Flower depth.*—35 mm to 45 mm.

*Buds.*—Number per spur: 1 or 2. Shape: Elongated. Length: 21 mm to 29 mm. Width: 12 mm to 14 mm. Color: Dark orange-red, closest to RHS 34 A. Scales: Typical to species, not distinguishing.

*Calyx.*—Depth: 25 mm to 30 mm. Diameter (funnel): 30 mm to 35 mm. Attitude: Semi-erect. Calyx lobes length: 9 mm to 11 mm. Calyx lobes width: 5 mm to 7 mm. Color: Dark orange-red, closest to RHS 32 A.

*Petals.*—Number per flower: 5 to 7. Size: Length: 19 mm to 24 mm. Width: 17 mm to 20 mm. Overall shape: Elliptical. Apex shape: Rounded. Base shape: Rounded. Surface (upper surface): Smooth. Surface (lower surface): Smooth. Margin: Entire, undulated. Mature color: Upper surface: Orange-red, RHS 33 A. Lower surface: Orange-red, RHS 33 A.

*Sepals.*—Number per flower: 5 to 7. Size: Length: 9 mm to 11 mm. Width: 5 mm to 7 mm. Overall shape: Triangular. Apex shape: Acute. Base shape: Fused. Surface (upper surface): Smooth. Surface (lower surface): Smooth. Margin: Entire. Mature Color: Outer surface: Orange-red, RHS 32 A. Inner surface: Orange-red, RHS 33 A.

*Pedicle.*—Flowers are sessile, no pedicle.

Fruit:

*Keeping quality.*—The fruit keeps well on the tree. It can be stored in cold temperature conditions at above 7° C. for about 4 weeks with good eating quality.

*Maturity when described.*—Ripe for commercial harvesting and shipment; beginning of October in Yizre'el Valley, Israel.

*Maturity period after full flowering.*—About 5 months after full flowering, beginning of May in Yizre'el Valley, Israel.

*Date of first picking (harvest).*—About October 1$^{st}$ in Yizre'el Valley, Israel in 2008.

*Type.*—Berry.

*General shape.*—Oblate, nearly uniform, symmetrical.

*Apex shape.*—Prominent crown of calyx segments at apex.

*Base shape.*—Symmetrical base, slightly flattened near stem end.

*Suture.*—None.

*Average weight.*—About 380 g.

*Fruit size.*—Average length (axial plane, without crown): 79 mm±1.0 mm. Average diameter (widest point, right angle to axial plane) 303 mm±3.0 mm.

*Crown.*—Height: 29 mm±1.0 mm. Circumference: 76 mm±2.0 mm. Lobes number: mostly 6 per fruit; Lobes position: half-closed to upright.

*Skin:*—Thickness: Medium. Surface: Smooth. Tendency to crack: Slight. Ground color: Dark pink. Blush color: Dark red, RHS 46 A. Percentage of skin surface with overcolor color: Uniformly spread over entire skin.

*Arils.*—Texture: Smooth and shiny. Length: 10 mm to 12 mm. Diameter: 5 mm to 7 mm. Weight (per aril): About 0.35 g. Volume (per aril): About 0.32 cm$^3$. Color at maturity: Dark red, RHS 46 A. Separation: Easy. Septum: Thin, transparent. Ripening: Uniform. Fibers: Not noticeable. Aroma: None. Eating quality: Very good. Juice production: Good. Flavor: Sweet-sour.

*Seeds.*—Overall shape: Ovate. Apex shape: Acute. Base shape: Rounded. Length: About 7.8 mm. Dry weight (per seed): About 0.026 g. Dry volume (per seed): About 0.04 cm$^3$. Hardness: Medium. Color (dry): White, RHS 155 C.

Reproductive organs:

*Androecium.*—Stamen: Number per flower: Numerous. Length: 5 mm to 6 mm. Color: Dark orange, RHS 33 B. Anther: Length: 5 mm to 6 mm. Color: Yellow, RHS 4 A.

*Pollination requirements.*—None, 'KAMEL' is self-fertile and self-pollinating.

*Gynoecium.*—Pistils: Number: One. Length: 5 mm to 10 mm. Diameter: About 1 mm. Color: Dark orange, RHS 33 B. Stigmas: Size: Very small. Color: Greenish-yellow, RHS 1 A. Ovary: Shape: Conical. Length: 8 mm to 9 mm. Diameter: 8-13 mm. Color: Red-orange, RHS 33 B. Pubescence: None.

Market: Fresh market and food, juice and dietary supplement manufacturing.

Usage: Fruit and extract.

Disease/pest resistance: No atypical resistance has been noted.

Disease/pest susceptibility: No atypical susceptibility has been noted.

Winter hardiness: Tolerant to temperatures down to −3° C. without observed damage to wood and buds of dormant pomegranate trees, under prevailing local conditions.

What is claimed is:

1. A new and distinct pomegranate variety of *Punica granatum* plant named 'KAMEL', as illustrated and described herein.

* * * * *